United States Patent
Weyl et al.

(10) Patent No.: US 6,883,363 B2
(45) Date of Patent: Apr. 26, 2005

(54) GAS SENSOR, IN PARTICULAR A LAMBDA PROBE, AND METHOD FOR PRODUCTION THEREOF

(75) Inventors: Helmut Weyl, Schwieberdingen (DE); Hans-Joerg Renz, Leinfelden-Echterdingen (DE); Lothar Diehl, Stuttgart (DE); Juergen Karle, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/344,391

(22) PCT Filed: May 31, 2002

(86) PCT No.: PCT/DE02/01986

§ 371 (c)(1), (2), (4) Date: Jul. 22, 2003

(87) PCT Pub. No.: WO02/101373

PCT Pub. Date: Dec. 19, 2002

(65) Prior Publication Data

US 2004/0011116 A1 Jan. 22, 2004

(30) Foreign Application Priority Data

Jun. 8, 2001 (DE) .......................... 101 27 917

(51) Int. Cl.$^7$ ............................. G01N 7/00; H01L 21/00
(52) U.S. Cl. .......................................... 73/23.2; 438/68
(58) Field of Search .............................. 73/23.2, 31.05, 73/31.06, 23.32, 23.31; 204/424, 425, 426, 427, 428, 429; 438/68, 71

(56) References Cited

U.S. PATENT DOCUMENTS

| 4,301,401 | A | * | 11/1981 | Roof et al. ................. 324/663 |
| 4,489,596 | A | | 12/1984 | Linder et al. |
| 4,604,161 | A | * | 8/1986 | Araghi ........................ 438/68 |
| 4,851,371 | A | * | 7/1989 | Fisher et al. .................. 438/21 |
| 4,958,514 | A | * | 9/1990 | Takami et al. ............. 73/25.03 |
| 5,228,975 | A | * | 7/1993 | Yamada et al. ............. 204/424 |
| 6,027,622 | A | | 2/2000 | Graser et al. |
| 6,083,371 | A | * | 7/2000 | Weyl et al. ................. 204/426 |
| 6,164,120 | A | | 12/2000 | Friese et al. |
| 6,179,989 | B1 | * | 1/2001 | Kennard et al. ............ 205/711 |
| 6,347,543 | B1 | * | 2/2002 | Geier et al. ................ 73/23.31 |
| 6,401,521 | B1 | * | 6/2002 | Nelson ...................... 73/31.05 |
| 6,546,783 | B2 | * | 4/2003 | Shirai ........................ 73/31.05 |
| 6,673,225 | B1 | * | 1/2004 | Arnold ....................... 204/547 |
| 6,737,668 | B2 | * | 5/2004 | Den et al. ....................... 257/9 |

FOREIGN PATENT DOCUMENTS

| DE | 44 36 580 | 4/1996 |
| DE | 197 51 424 | 11/1998 |
| DE | 199 37 160 | 3/2001 |
| EP | 0 704 698 | 4/1996 |

\* cited by examiner

Primary Examiner—Michael Cygan
(74) Attorney, Agent, or Firm—Kenyon & Kenyon

(57) ABSTRACT

The ceramic sensor body, held inside a housing by a sealing packing, is provided with a circumferential coating of an electrically insulating material in the region of the sealing packing, so that the sensor body remains potential-free with respect to the housing, even when a sealing packing is used that is made of a material having poor electrical insulating qualities. In this manner, a glass putty is used for the sealing packing, which, while having comparatively poor insulating characteristics, provides a good sealing effect at high loading capacity.

5 Claims, 2 Drawing Sheets

GAS SENSOR, IN PARTICULAR A LAMBDA PROBE, AND METHOD FOR PRODUCTION THEREOF

This application is a National Stage Application filed under 35 U.S.C 371 of International Application Number PCT/DE02/01986, filed 31 May 2002.

FIELD OF THE INVENTION

The present invention relates to gas sensors, such as, for example, lambda sensors, which include a ceramic sensor body and an associated housing. A sealing packing, surrounding the sensor body at a midsection and supporting it, subdivides the housing into a measuring gas chamber, acted upon by a measuring gas, and a reference-gas chamber, able to be acted upon by a reference gas, such as, for example, by air of the atmosphere.

BACKGROUND INFORMATION

Exhaust systems of modern internal combustion engines, such as, for example, those for motor vehicles, may be regularly provided with catalytic converters for converting harmful exhaust gases into harmless reaction products. In order for the catalytic converters to function well, it may be required to feed air and fuel to the engine in a predefined proportion. The engine controls provided for this purpose may be connected on their input side to a so-called lambda probe whose signals represent the composition of the exhaust gas and thus may enable the engine control to adjust the ratio of fuel and combustion air in a manner optimal for the catalytic converter.

Modern heating devices in which fuels are burned to generate heat may work similarly.

The sealing packing mentioned in the introduction may have a plurality of functions. For example, in the housing of the sensor body, it may separate a measuring gas chamber or an exhaust-gas chamber from a reference-gas chamber. Additionally, it may also support the sensor body in the housing, whose inner cross-section may have a shape that deviates from the outer cross-section of the sensor body. Furthermore, the sealing packing may keep the sensor body electrically potential-free, or may insulate it electrically from the housing, which may be made of metal.

The sealing packing may be built up from a plurality of layers, the different layers assuming various main functions, such as protecting the remaining layers from pulsations of the exhaust gas, firmly supporting the sensor body in the housing, and sealingly separating the exhaust-gas chamber and the reference-gas chamber from one another.

A steatite-pressure packing into which a boron nitride disk is inserted may provide the sealing separation of the measuring gas chamber or exhaust gas chamber and the reference gas chamber with respect to one another. This may ensure good electric insulation between the sensor body and the associated housing and good sealing from gasoline vapors or fuel vapors as well as liquid fuel.

However, the required manufacturing effort may be relatively high.

SUMMARY OF THE INVENTION

According to an exemplary embodiment of the present invention, the sensor body may be provided with a coating of an electrically insulating material in the region of the sealing packing or inside the sealing packing, so that even materials having poor insulating properties may be used as sealing packing for the purpose of separating the exhaust gas chamber and the reference gas chamber from one another.

The sensor body may be kept electrically insulated by an insulating layer located on the sensor body so that a sealing packing with good electrical insulating properties may not be required and, in this manner, greater constructive freedom may be offered in the choice of materials for the sealing packing.

In doing so, the insulating layer on the sensor body in the region of the sealing packing may be produced simultaneously with the electrically insulating coatings of the sensor body at its electrodes. Since these may be required anyway, practically no additional production effort may be required.

A glass putty may readily be used as a result of the present invention, which, at comparatively lower cost, may provide at least the same, but potentially considerably better sealing than boron nitride.

DETAILED DESCRIPTION

Figure 1:
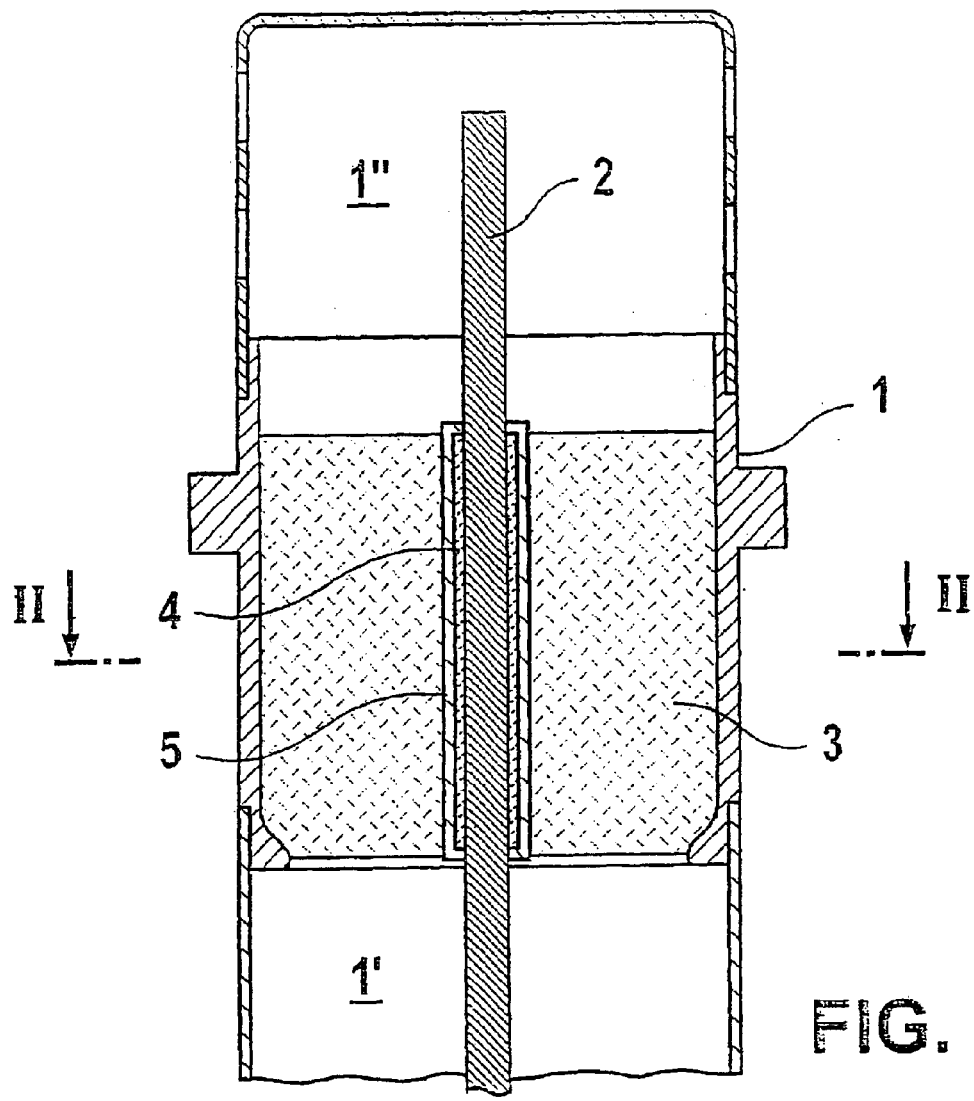
FIG. 1 shows a schematized longitudinal section of a sensor body and the associated housing as well as the sealing packing.
Figure 2:
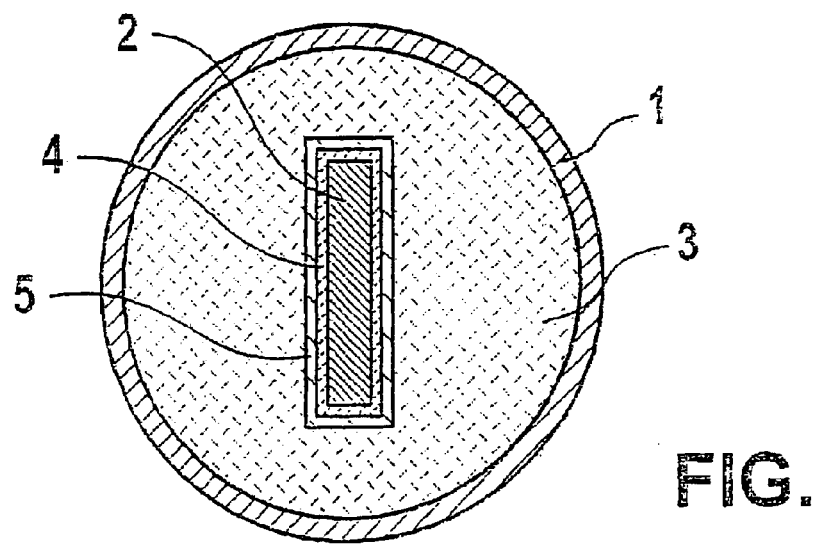
FIG. 2 shows a sectional view according to cut line II—II in FIG. 1.

According to FIGS. 1 and 2, a sensor body 2, in the form of a ceramic laminate, is securely accommodated in an essentially tubular housing 1 and supported in housing 1 by a sealing packing 3. Sealing packing 3 divides the interior of housing 1 into a reference gas chamber 1', as well as an exhaust gas chamber or measuring gas chamber 1", associated end regions of sensor body 2 extending into both chambers.

At its end assigned to reference gas chamber 1', housing 1 is open, so that electrical connection lines (not shown) may be connected to electrodes at the sensor body. The part of housing 1 surrounding the exhaust gas chamber is provided with one or a plurality of smaller openings, via which the exhaust gas chamber or measuring gas chamber 1" communicates with the exterior of housing 1. By this housing section, housing 1 projects into an exhaust branch of an internal combustion engine or heating device, sealing packing 3 sealing the exhaust branch with respect to the atmosphere.

According to an exemplary embodiment of the present invention, sensor body 2, in the region of sealing packing 3, includes a circumferential layer 4 of electrically insulating material. This may keep sensor body 1 potential-free even with respect to housing 1, which may be made of metal, if the material of sealing packing 3 is electrically conductive to a more or less pronounced degree, or has only poor electrical insulating properties.

As a result of electrically insulating circumferential layer 4, sealing packing 3, completely or in part, may be in the form of glass putty, whose electrical insulating resistance drops to approx. 200 kΩ when the temperature of the housing rises to approximately 530 degrees C., analogously to the temperature in the exhaust branch.

Such a glass putty may provide excellent sealing from fuel in liquid or vapor form, such as, for example, from gasoline. If required, an additional thin sealing layer or foil may also be provided within the glass putty, made of boron nitride, for example. Such a thin sealing layer or sealing foil may be less expensive than the thick boron nitride layer that may have been used until now.

To improve the sealing between sealing packing 3 and sensor body 2, a sealing layer 5, made of metal, for example, may also be provided on the electrically insulating circumferential layer 4 of the sensor body.

Figure 3:
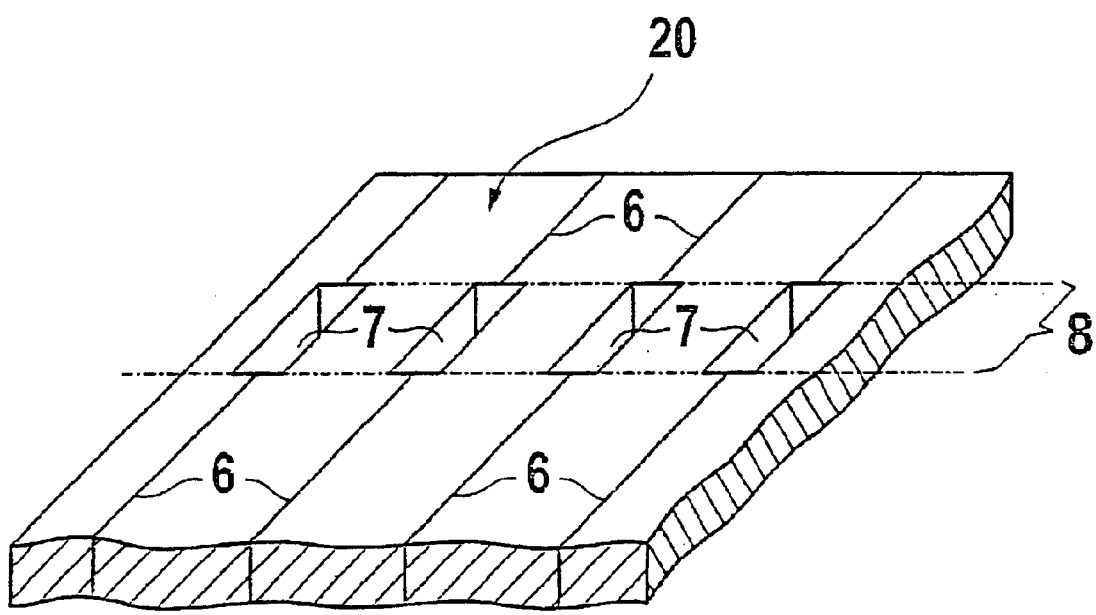
FIG. 3 shows exemplary production steps for the insulation coating of the sensor bodies in the region for the sealing packing.

An exemplary method of producing the electrically insulating peripheral layer 4 is explained with the aid of FIG. 3.

To manufacture a great number of sensor bodies 2, a large-surfaced, patterned ceramic laminate 20 is produced, which may be divided into many sensor bodies 2 by cutting along cutting lines 6.

In the area of circumferential layers 4 to be produced, slits 7, which penetrate the aforementioned laminate from its upper side to its lower side, are punched out in the large-surfaced laminate. Subsequently, a strip 8 made of an electrically insulating material may be applied using printing technology, this material also penetrating into slits 7 or being introduced into slits 7 by underpressure or similar exemplary methods. Then, the large-surfaced ceramic laminate is separated along cutting lines 6, the insulation material that has penetrated into slits 7 being cut through. As a result, each sensor body 2, while forming an electrically insulating circumferential layer 4, is covered by insulating material both on its upper as well as its lower side and along its longitudinal edges.

This is followed by a sintering process during which sensor bodies 2, which have been cut out from laminate 20, are hardened together with the insulating material.

Sensor bodies 2 may be separated from one another at cutting lines 6 when slits 7 are stamped out. During the subsequent application of the insulating material, sensor bodies 2, having been separated from one another, may be required to then be held in position by appropriate measures or tools.

The application of strips 8 made of electrically insulating material may occur simultaneously with the application of electrically insulating layers (not shown) at additional areas of the large-surfaced laminate, or of sensor bodies 2, for example, at electrode surfaces on sensor bodies 2.

Figure 4:
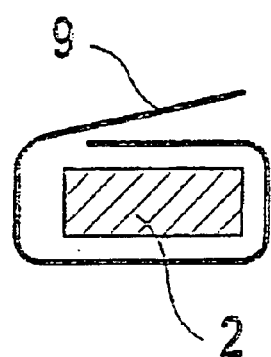
FIG. 4 shows an additional exemplary manner of producing this insulation layer.

To produce the electrically insulating layer 4; an electrically insulating tape 9 may be wrapped around the sensor bodies according to FIG. 4. In its place, a transfer tape carrying the insulation material may be used, which, as a result of a subsequent high-temperature process, is dissolved or destroyed on the respective sensor body 2 during simultaneous sintering of the insulation material.

To produce sealing layer 5, other exemplary methods may be used that are essentially equivalent to those used to produce electrically insulating circumferential layer 4.

What is claimed is:

1. A method of for manufacturing gas sensors with sensor bodies, comprising:

producing a flat laminate separable into the sensor bodies at cutting lines;

one of producing and stamping out slits that penetrate the flat laminate along the cutting lines in areas of the flat laminate provided for a coating with an electrically insulating material; and filling the areas with the electrically insulating material with an application of the electrically insulating material on at least one of an upper and a lower side of the flat laminate within a strip which covers the slits in a transverse direction;

wherein the slits penetrate the flat laminate from the upper side of the flat laminate to the lower side of the flat laminate.

2. The method according to claim 1, further comprising:

separating the flat laminate at the cutting lines prior to a sintering process.

3. The method of claim 2, further comprising:

separating the flat laminate at the cutting lines after application of the electrically insulating material.

4. The method of claim 1, further comprising:

sintering the sensor bodies with the electrically insulating material.

5. A method of for manufacturing gas sensors with sensor bodies, comprising:

producing a flat laminate separable into the sensor bodies at cutting lines;

one of producing and stamping out slits that penetrate the flat laminate along the cutting lines in areas of the flat laminate provided for a coating with an electrically insulating material; and filing the areas with the electrically insulating material with an application of the electrically insulating material on at least one of an upper and a lower side of the flat laminate within a strip which covers the slits in a transverse direction;

wherein the slits are stamped out.

* * * * *